United States Patent [19]

Korn

[11] 4,307,730

[45] Dec. 29, 1981

[54] APPARATUS FOR PULMONARY FUNCTION ANALYSIS

[75] Inventor: Volker Korn, Nuremberg, Fed. Rep. of Germany

[73] Assignee: Siemens Aktiengesellschaft, Berlin & Munich, Fed. Rep. of Germany

[21] Appl. No.: 132,884

[22] Filed: Mar. 24, 1980

[30] Foreign Application Priority Data

Mar. 29, 1979 [DE] Fed. Rep. of Germany ....... 2912391

[51] Int. Cl.³ .............................................. A61B 5/08
[52] U.S. Cl. .................................................. 128/728
[58] Field of Search ............... 128/716, 719, 720, 725, 128/727, 728, 730

[56] References Cited

U.S. PATENT DOCUMENTS

| | | | |
|---|---|---|---|
| 3,527,205 | 9/1970 | Jones | 128/725 |
| 3,659,590 | 5/1972 | Jones et al. | 128/725 |
| 4,127,115 | 11/1978 | Franetzki | 128/725 |

FOREIGN PATENT DOCUMENTS

| | | | |
|---|---|---|---|
| 2541691 | 3/1977 | Fed. Rep. of Germany | 128/719 |
| 203834 | 1/1968 | U.S.S.R. | 128/716 |

OTHER PUBLICATIONS

Green et al., "A Simplified Closing Volume Method . . . ", The Lancet, Oct. 28, 1972, pp. 905–906.

*Primary Examiner*—Lee S. Cohen
*Attorney, Agent, or Firm*—Hill, Van Santen, Steadman, Chiara & Simpson

[57] ABSTRACT

For the measurement of functional respiratory volume, or respiratory capacities, apparatus are known including a respiratory bag which can be connected to a respiratory tube via a first valve system and which can be connected to test gas receptacles via an additional valve system and which exhibit gas analysis devices for measurement of the test gas concentration in the respiratory bag. Precise concentration measurements have been hitherto possible only discontinuously with chemical methods, or continuously with a large apparatus outlay (mass spectrometer). By way of a contrast, simple thermal conductivity sensors are unsatisfactory in measuring precision. According to the present disclosure, the concentration determination proceeds by means of a gas analysis device through continuous density determination of the mixture of test gas and respiratory air in the respiratory bag, for which purpose a measuring probe can be introduced into the respiratory bag by means of a separate connection, and the gas density-dependent measuring signal corresponding to the present test gas concentration, which signal has been tapped at the measuring probe can be directly displayed as the pulmonary function measured value (RV, FRC). In this manner the determination of respiratory volumes, or respiratory capacities, respectively, is substantially simplified.

11 Claims, 6 Drawing Figures

APPARATUS FOR PULMONARY FUNCTION ANALYSIS

BACKGROUND OF THE INVENTION

The invention relates to an apparatus for pulmonary function analysis, in particular, for measurement of functional respiratory volumes, or respiratory capacities, respectively, comprising a respiratory bag which can be connected to the examination subject via a first valve system by means of a respiratory tube, and which can be connected to a test gas receptacle via an additional valve system, or the like, and comprising a gas analysis device for measurement of the test gas concentration in the respiratory bag.

In order to determine functional respiratory volumes and/or respiratory capacities, for example, nitrogen washouts of the lungs are being carried out up to the present time. To this end, volume measurements, for example, with a spirometer, on the one hand, and concentration measurements of the respiratory gas, on the other hand, are necessary. An apparatus for carrying out such nitrogen-washouts is already prior knowledge, in which the volume measurement is simplified and only a precise nitrogen concentration measurement need still be carried out. This concentration measurement, subsequent to washout of the nitrogen, proceeds discontinuously therein on the part of partial specimens, removed from the respiratory bag, by means of chemical methods.

In addition to the special nitrogen-washouts of the lungs, for the same measuring purpose, wash-ins of defined test gas quantities, preferably inert gases, into the lungs are also known. Measured quantities are here essentially the initial- and end-concentration of the test gas. Thus, again, as precise as possible a concentration measurement is desired for which purpose corresponding gas analysis devices are necessary. In the known apparatus the concentration measurement proceeds by means of determination of the thermal conductivity which determination is, however, rather imprecise in the case of utilization of inert gases, so that the pulmonary function analysis remains unsatisfactory.

SUMMARY OF THE INVENTION

Accordingly, the object underlying the invention resides in producing an apparatus for pulmonary function analysis which is simply constructed, exhibits no complicated gas analysis devices, but which renders possible information which is as precise as possible regarding the pulmonary function.

In the case of an apparatus of the type initially cited, the object is achieved in accordance with the invention in that the concentration measurement proceeds by means of a gas analysis device through continuous determination of the density of the mixture of test gas and respiratory air in the respiratory bag, for which purpose, by means of a separate connection, a measuring probe can be introduced into the respiratory bag, and that the gas density-dependent signal, corresponding to the present test gas concentration, which signal is tapped with the probe, can be directly represented as the pulmonary function measured quantity.

Thus, in the case of an apparatus in accordance with the invention, as a measure of the gas concentration, the gas density in the respiratory bag is continuously measured and displayed directly on a recorder (or registering apparatus). Such gas density curves can already be directly utilized for the purpose of pulmonary function analysis. In conjunction with an additional volume measurement, the respiratory volumes, such as also, as a particularly interesting measured quantity, the residual volume (RV), can be determined therefrom. Likewise the functional residual capacity (FRC) can be determined; the relation between these quantities will be apparent from the disclosure relating to the fifth figure of drawings herein.

Whereas, in the known apparatus, for a satisfactorily precise concentration measurement, either discontinuous chemical methods were employed, or, however, for continuous measurement, a costly mass spectrometer was necessary, the measuring probe employed in the inventively designed apparatus is constructed extremely simply.

Therefore, the apparatus for pulmonary function analysis thus produced is extremely simple according to construction and method of operation; a portion of the apparatus components can also be introduced for other measuring purposes in the framework of the pulmonary function test. If, as test gas receptacles, disposable cartridges having a defined test quantity of known concentration are utilized, from which a known test gas quantity is directly conducted into the respiratory bag, a mobile measuring installation results without the gas bottles which have hitherto hampered the transport of the equipment.

Further advantages and details of the invention shall be apparent from the following detailed description of various exemplary embodiments on the basis of the accompanying sheets of drawings; and other objects, features and advantages will be apparent from this detailed disclosure and from the appended claims.

BRIEF DESCRIPTION OF THE DRAWINGS

FIG. 3 illustrates a measuring arrangement, modified in relation to FIG. 2, for the purpose of complete test gas wash-in;

DETAILED DESCRIPTION

Figure 1:
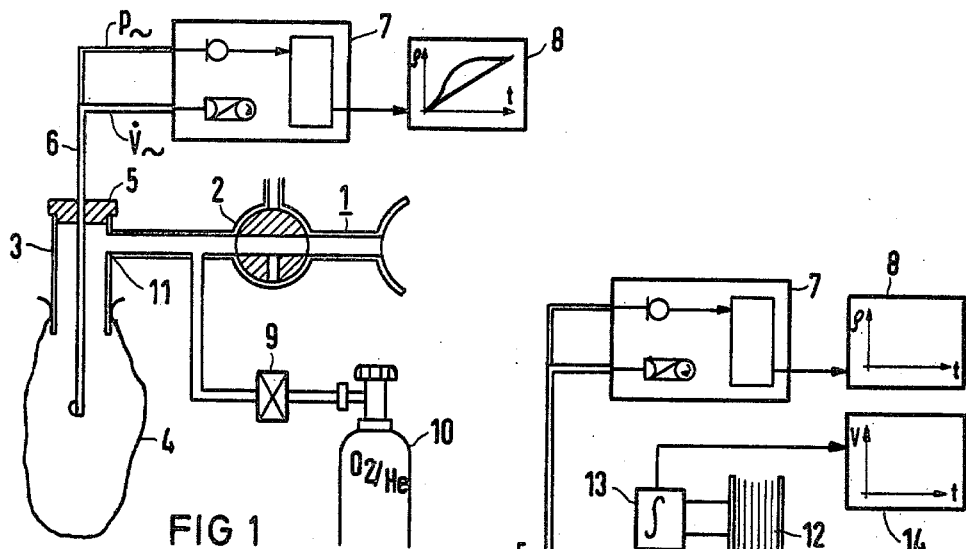
FIG. 1 schematically illustrates a measuring arrangement for determining the wash-in time of test gases.

In FIG. 1, reference numeral 1 designates a respiratory tube with a mouthpiece connection for an examination subject. Adjacent the mouthpiece end of the respiratory tube 1 there is a three-way valve 2, via which the test subject can breathe exterior air (room air) as needed. The end of the respiratory tube remote from the mouthpiece is designed as a junction fitting 3. At an open end of the fitting 3 a respiratory bag 4 is arranged. An opposite end of the fitting 3, disposed opposite the open end, is provided with a closure (or seal) 5 through which a measuring probe 6 can be introduced into the respiratory bag 4. The measuring probe 6 consists of a hollow tube for the purpose of impressing an alternating flow ($\dot{v}\sim$) of a known amplitude and frequency, and at which, in proximity to the open end of the hollow tube within the respiratory bag 4, the alternating pressure (p$\sim$) is tapped. The flow line and the pressure measuring line of the measuring probe 6 are connected outside the respiratory bag 4 to an operational apparatus 7 which generates a defined alternating flow ($\dot{v}\sim$), on the one hand, and measures the detected alternating pressure amplitude (p$\sim$) as an electrical signal, on the other hand, processes it electronically and supplies a corresponding analog signal. This analog density signal is capable of representation as a time function on a recorder (or registering device) 8. Via a reducing valve 9 it is possible to supply test gas from a gas bottle 10 to the respiratory bag 4 via a connection 11. The gas connection 11 is arranged on the respiratory tube 1 or directly at the fitting 3.

In order to carry out the pulmonary function analysis, with a closed three-way valve 2 (the valve 2 being turned 90° counterclockwise from the position shown in FIG. 1), via the reducing valve 9, a desired quantity of the test gas mixture from the gas bottle 10 is filled into the respiratory bag 4. Subsequently, the test subject breathes into the respiratory bag 4 (with valve 2 in the position shown in FIG. 1), inhaling and exhaling for approximately 1 to 3 minutes, during which the gas density signal is continuously recorded (or plotted) by the recorder 8. In the case of examination subjects with a normal pulmonary function, the signal will initially rapidly increase, and after approximately one minute, will run asymptotically into a saturation condition. By contrast, in the case of pathological conditions, the gas density signal increases slowly; and an asymptotical saturation condition is not reached in certain instances. A distribution malfunction is present which makes an exact measurement of the residual volume necessary.

Figure 2:
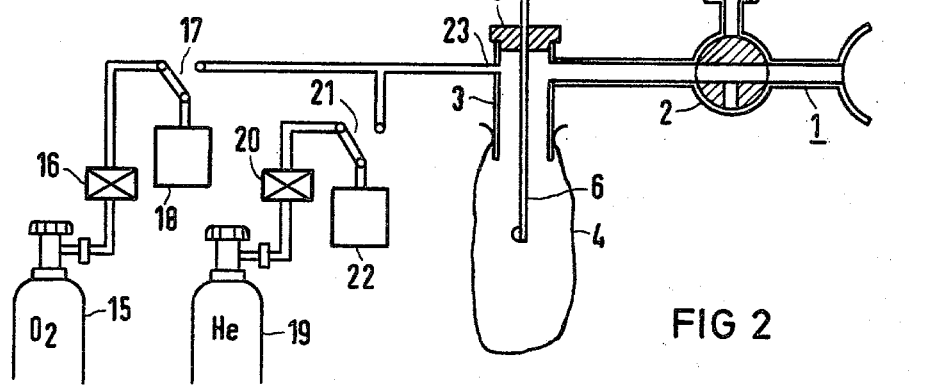
FIG. 2 schematically illustrates a measuring arrangement for determining the residual volume, or the functional residual capacity, respectively.

In FIG. 2, reference numeral 1 again denotes a respiratory tube with a three-way valve 2 leading to the mouthpiece end, and with a fitting 3 at the other end for a respiratory bag 4 as well as a measuring probe 6 capable of being introduced therein. The measuring probe 6, in turn, is connected to the operational apparatus 7 from which the density measuring signal is delivered to the recorder 8. At the three-way valve 2 a spiroceptor 12 for respiratory flow measurement is furthermore connected from which, via an integrator 13, the respiratory volume V is delivered to an additional recorder 14 for recording. Instead of the spiroceptor 12 with integrator 13, a closed spirometer can also be employed. Via a line system, test gas receptacles can be connected to the respiratory bag 4. In detail, for this purpose, overpressure gas bottles 15 and 19 are connected, via reducing valves 16 and 20 and pneumatic conduit switches 17 and 21, with intermediate volumes 18 and 22, whereby, subsequent to pressure reduction to approximately three bar, the defined volumes 18 and 22 are in each instance capable of being filled with the test gases. Via the pneumatic changeover switches 17 and 21 the test gas volumes are fed into the respiratory bag 4 via a gas inlet 23. Expediently, the first overpressure gas bottle 19 contains pure helium, and the second bottle 15 contains pure oxygen, so that, in the respiratory bag 4, desired test gas quantities of a defined test gas composition can be readily adjusted.

For the determination of the FRC (functional residual capacity) in this case, in addition to the quantitative concentration-measured values, also the filled-in volume is necessary as operand. The helium balance results in the following relation:

$$V_1 \cdot X_1 = (V_1 + V_o + FRC) \cdot X_2 \qquad (1)$$

whereby $V_1$ signifies the test gas volume filled in from the gas bottles 15 and/or 19, $V_o$ signifies the fixed system volume (dead space), and FRC signifies the desired residual capacity. $X_1$ and $X_2$ are the respective helium concentrations. If air from the respiratory bag 4 is inhaled and exhaled by the test subject, the relative change in the gas density is less than that of the thermal conductivity. Therefore, by inhaling and exhaling a test gas mixture which is clearly lighter due to the helium concentration, every density change of the gas mixture in the respiratory bag 4 can be directly detected as a change in the helium concentration. Since it is possible to proceed from a strictly linear relationship between the density and the signal voltage on the operational apparatus 7 for the measuring probe 6, it is possible to dispense with the absolute determination of the gas concentration. The recording of the output signals of the operational apparatus 7 on the recorder 8 for the bag gas ($U_B$), the mixed gas ($U_M$) and for normal air ($U_L$) suffices. Thus, from equation (1) there follows:

$$FRC = V_1 \cdot [(U_M - U_B/(U_L - U_M)] - V_o \qquad (2)$$

The test subject first breathes room air via the spiroceptor 12 (with valve 2, FIG. 2, turned clockwise ninety degrees from the position shown in FIG. 2). The respiratory volume curve is recorded on the recorder 14. After filling-in the defined test gas volume $V_1$ with a concentration $X_1$ into the respiratory bag 4, the test subject is connected to the respiratory bag 4, given a breathing situation corresponding to the desired quantity. After a relatively brief inhaling and exhaling time (approximately 1 to 5 minutes) the test subject can be separated from the system at a desired respiratory situation. The value FRC then directly results from equation (2) with the values read off for $U_B$, $U_M$ and $U_L$.

Figure 3:
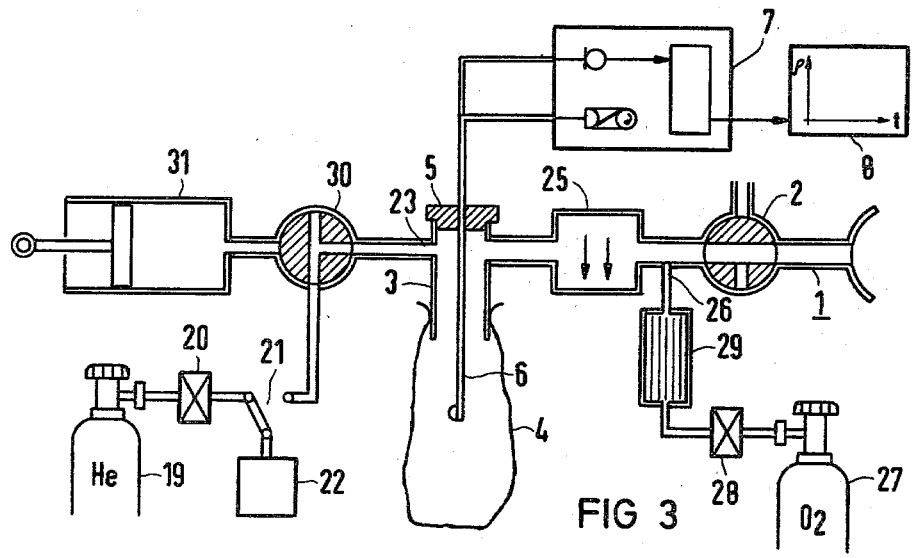

In FIG. 3, the exemplary embodiment according to FIG. 2 is modified in such a manner that inhaling and exhaling into the respiratory bag 4 can be carried out to the point of complete helium wash-in into the lungs. Such a complete wash-in can last up to ten minutes. In the case of such longer inhaling and exhaling into the respiratory bag 4, a $CO_2$-absorption from the respiratory gas as well as subsequent oxygen supply for the test subject is necessary. For this purpose, a $CO_2$ absorber 25 is connected between the three-way valve 2 and the respiratory bag 4. Via a gas inlet 26, pure oxygen is dispensed from a gas bottle 27 with a reducing valve 28 and a flow meter 29 into the respiratory tube 1 for the test subject.

A spirometer for respiratory flow or respiratory volume measurement, respectively, is not present in the exemplary embodiment according to FIG. 3. In this case, also only an overpressure gas bottle 19 with reducing valve 20 is provided with which, via the pneumatic change-over switch 21 and standard volume receptacle 22, pure helium is filled into the respiratory bag 4. Via a valve 30 with a manually actuated mechanical plunger pump 31 the mixed gas can be withdrawn from the respiratory bag 4 and in this fashion the bag volume can be ascertained at the conclusion of a measurement.

If one proceeds using pure helium as the test gas, the following helium balance results corresponding to equation (1):

$$V_{He} = (V_2 + V_o + FRC) \cdot X_2 \qquad (3)$$

whereby, in addition to the already known values, $V_{He}$ signifies the volume of the pure helium gas, and $V_2$ signifies the volume in the respiratory bag after completed measurement (thus a complete helium-wash-in).

In order to conduct the measurement, a defined helium volume $V_{He}$ is filled into the respiratory bag 4, a random oxygen- or air-component is filled-in in addition, and the test subject, after expiration, is connected to the respiratory bag 4. The test subject now breathes until the final density has been asymptotically attained on the recorder 8. During this possibly longer inhaling and exhaling time, the carbon dioxide is absorbed in the absorber 25 in the expiration phase. For the breathing of required oxygen, supply is provided in a suitable fashion from the gas bottle 27.

Figure 4:
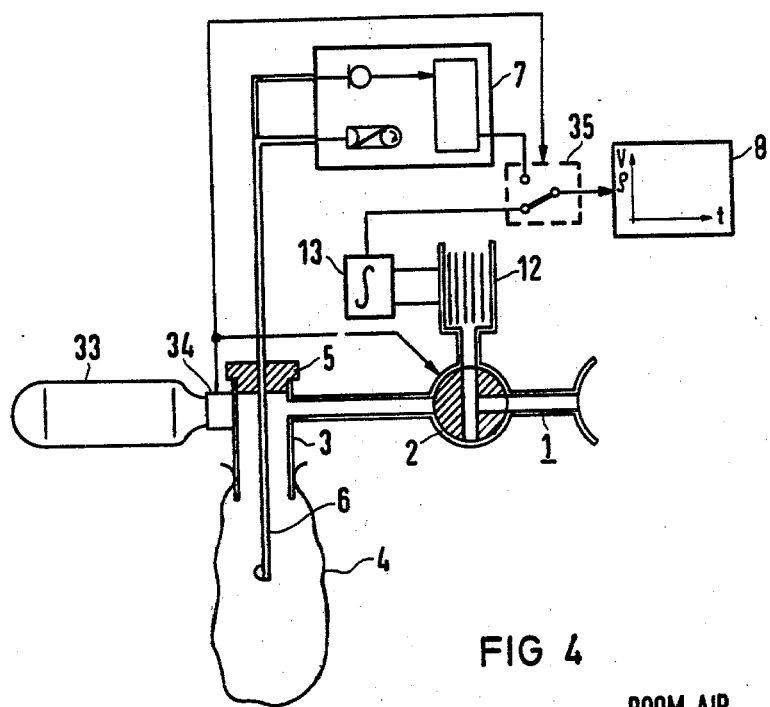
FIG. 4 illustrates a measuring arrangement, further modified in relation to FIG. 2, designed as a mobile unit.

The measuring construction according to FIG. 4 is modified in relation to the construction in FIG. 2 in such a manner that the recorder 8 can be alternatively connected to the concentration signal transmitter or the volume signal transmitter via a selector switch 35. Instead of the overpressure gas receptacles now one-way gas cartridges 33 are connected to the respiratory bag 4. Such gas cartridges 33 contain, for example, one liter of a test gas at 5 bar; thus they deliver five liters at atmospheric pressure. This quantity is suitable for a measurement. With connection of the cartridge 33 to the connection designed as an inlet valve 34, the three-way valve 2 in the respiratory tube and the selector switch 35 are simultaneously changed over via an electric feedback control system. Thus, the entire measuring operation is largely automated.

Figure 5:
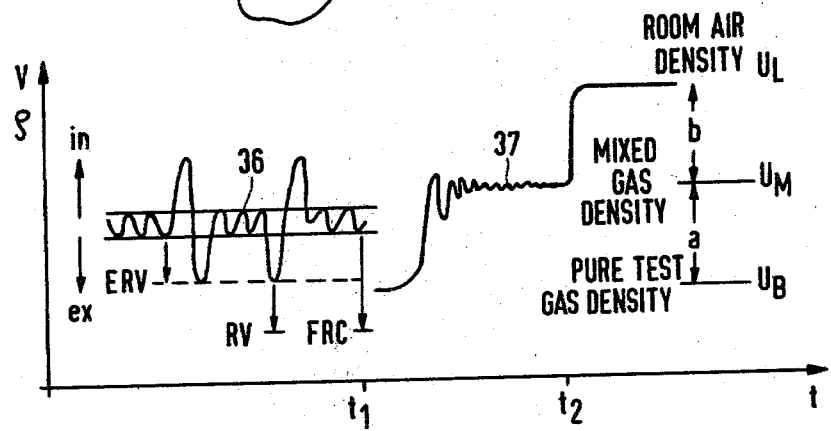
FIG. 5 illustrates recording curves for the purpose of pulmonary function analysis which were recorded with the use of apparatus according to FIG. 2 or 4, respectively.

In FIG. 5, 36 denotes a respiratory volume curve of a test subject and 37 denotes a density measuring curve corresponding to the concentration progression (or course) in the respiratory bag 4 during a measurement. The respiratory volume curve 36 reproduces a number of inspiratory and expiratory respirations, whereby the test subject breathes with normal respiratory volume (AV). The significant pulmonary function measured quantities are the residual volume (RV) and the functional residual capacity (FRC). The two quantities are distinguished from one another by the expiratory reserve volume (ERV). Depending upon in what respiratory situation the measurement is initiated with the inventive apparatus, the corresponding respiratory volume, or respiratory capacity respectively is determined as the pulmonary function measured quantity. It can be advantageous, in the case of a measuring construction according to FIGS. 1 through 4, to associate with a spiroceptor as the respiratory flow signal transmitter, a microprocessor by means of which the measurement is controlled in a specified desired respiratory situation. In the case of the measured quantity output it is then possible to directly differentiate into RV and FRC.

In FIG. 5, the switch 35 according to FIG. 4 is initially switched to respiratory volume recording. With connection of the test gas cartridge 33 to the respiratory bag 4, given the desired respiratory situation, a switchover is effected to bag respiration and simultaneously the recorder 8 is switched over to density display. The density signal initially rapidly increases from the pure test gas value $U_B$ in order to, with constant inhaling and exhaling, to oscillate to the asymptotical value $U_M$.

From the signal structure, the individual respiratory cycles are still recognizable. If the limit value has been attained the flexible respiratory bag 4 can be removed from the tube fitting 3. The density signal tapped at the measuring probe 6 is then immediately adjusted to air value $U_L$. In the recording curve 37, the differences between the relative signal values are designated with $$U_M - U_B = a$$

$$U_L - U_M = b$$

so that equation (2) can be correspondingly written $$FRC = V_1 \cdot (a/b) - V_o \qquad (2a)$$

Since $V_o$ is kept as small as possible and is constant for a selected measuring construction, this value can be ignored, or calibrated-in, respectively. From the ratio a/b, which can be directly read-off from the recording curve 37, the desired measured value results.

With the invention described on the basis of the exemplary embodiments, the determination of pulmonary function measured values is possible in the simplest fashion. In particular, through utilization of the hollow tube subjected to a defined alternating flow, as a gas density measuring probe capable of introduction in the respiratory bag, and measurement of the alternating pressure amplitude at the hollow tube, costly concentration measurements of test gas components are superfluous. Specifically for helium as the test gas component a sufficient sensitivity of the gas density signal as the measure of concentration results when the alternating pressure is tapped in proximity of the open end of the hollow tube 6. Good results were obtained with the utilization of hollow tubes 6 with a diameter between two and five millimeters (2 and 5 mm), an alternating flow with an alternating flow amplitude between ten and fifty milliliters per second (10 and 50 ml/s) and a frequency between ten and one hundred hertz (10 and 100 Hz), whereby the spacing of the pressure measuring location from the hollow tube open end was selected to be less than the inner diameter of the hollow tube.

It will be apparent that many modifications and variations may be effected without departing from the scope of the novel concepts and teachings of the present invention.

Further details of construction and operation of the density measuring component 7 are found in U.S. Pat. No. 4,127,115 issued Nov. 28, 1978, and the disclosure of this patent is incorporated herein by reference, by way of background. A commercially available product of the common assignee of such patent and the present application is known as the SIREGNOST FD5. Further background concerning this instrument may be had by reference to the article: Smidt, U.; Löllgen, H; Nieding G.; Franetzki, M.; Korn, V.; Prestele, K.; A new oscillation method for determining resistance to breathing. Progr. Resp. Res. 6 (1976), 402.

Figure 6:
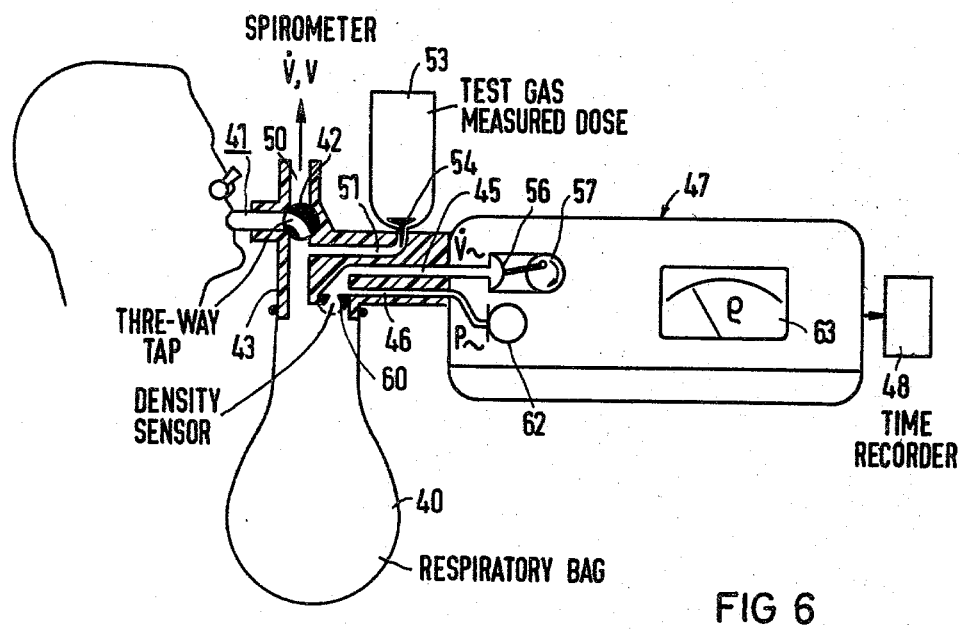
FIG. 6 is a diagrammatic illustration of a measuring arrangement wherein the measuring probe is an integral part of the fitting which receives the respiratory bag.

Description of FIG. 6.

In FIG. 6, a respiratory bag is indicated at 40 and is shown as being associated with a respiratory tube 41, a valve 42, a fitting 43, a density measuring probe passage 45 having a pressure sensing passage 46, an operation apparatus 47, and a recording apparatus coupled therewith as indicated at 48.

The fitting 43 is further shown as including a passage 50 leading to a spirometer arrangement such as indicated at 12, 13, 14 in FIG. 2, and a narrow passage 51 leading to a test gas overpressure recepticle 53 with a controllable valve means 54 corresponding to the elements 33, 34 of FIG. 4.

The apparatus 47 like the apparatus 7 of the previous embodiments may include a diaphragm pump schematically indicated at 56 which is reciprocated by means of a rotary drive indicated at 57 so as to impress an alternating flow of known amplitude and frequency onto the passage 45 which is coupled with the interior of the respiratory bag 40 via a metering orifice as indicated at 60. *The pressure sensing passage 46 couples the alternating pressure which is tapped at the passage 45 to a suitable pressure transducer as indicated at 62. The pressure transducer 62 may supply a continuous analog electrical signal as a function of the alternating pressure in the passage 45 relative to the external pressure external to the bag 40.

*The orifice is annular with an inner diameter of approximately 3 mm and with sharp edges.

It will be apparent that with the valve 42 shifted approximately 90° in the clockwise direction, a volume recorder such as indicated at 14 in FIG. 2 can record volume curves such as indicated in FIG. 5 at 36. With the valve 42 shifted from the position shown in FIG. 6 by approximately 90° in the counterclockwise direction, the bag 40 can be filled with a test gas such as helium, so that the test gas occupies a pre-determined volume $V_1$ at atmospheric pressure. The valve 42 may then be shifted to the position shown in FIG. 6, whereupon a density curve such as indicated at 37 in FIG. 5, may be taken by means of a recorder such as indicated at 8 connected with the output means 48 of FIG. 6. FIG. 6 may, of course, be modified to incorporate any of the features of FIGS. 1-4. Reference is made to U.S. Pat. No. 4,127,115 for detailed examples as to the configuration of the metering orifice 60 for use in conjunction with the present invention.

I claim as my invention:

1. Apparatus for pulmonary function analysis, comprising:

respiratory bag means for receiving a test gas, mouthpiece means for receiving the mouth of a patient, a valve system controlling fluid connection of said mouthpiece means with said respiratory bag means, gas supply means for supplying test gas to said respiratory bag means, density measuring means coupled with respiratory bag means, means for filling said respiratory bag means with a test gas from said gas supply means and for operating said density measuring means to register a test gas density value ($U_B$) repesenting the density of the test gas in said respiratory bag means, and means comprising said valve system for connecting said mouthpiece means with said respiratory bag means after the filling thereof with said test gas and for operating said density measuring means to register a succession of values of the density of the test gas and respiratory air in said respiratory bag means as a patient inhales and exhales until an equilibrium value ($U_M$) of density is registered at said density measuring means, whereby in conjunction with a measured value of the density of room air ($U_L$), a measure of at least one of functional respiratory capacity (FRC) and residual volume (RV) is defined.

characterized in that the density measuring means comprises a measurement passage, means coupled with said measurement passage for impressing a defined alternating flow ($\dot{v}\sim$) of a known frequency on the respiratory bag means, and means whereby the alternating pressure ($\dot{p}\sim$) developing in the measurement passage relative to the external pressure is measured as the gas density-dependent signal.

2. Apparatus according to claim 1, characterized in that said density measuring means comprises pressure sensing means tuned to the frequency of said alternating flow for supplying a continuous gas-density dependent analog signal.

3. Apparatus according to claim 1, with said density measuring means having a recorder (8) connected therewith for recording the density $U_B$ of the test gas in said respiratory bag means, said density measuring means supplying an analog signal to said recorder as a function of the density as the patient inhales and exhales so that the recorder provides a record of the equilibrium value $U_M$ for the test gas and other gases in the system, and means for supplying room air to the density measuring means such that the recorder records a room air density value $U_L$ along with the values $U_B$ and $U_M$.

4. Apparatus according to claim 2, with said gas supply means being operable to accommodate several test gas receptacles (15,19) with different test gases, and said valve system comprising means for controlling the supply of test gas from each of a plurality of test gas receptacles to said respiratory bag means.

5. Apparatus according claim 4, with said gas supply means having a plurality of overpressure gas receptacles (15, 19) connected therewith, and said gas supply means having respective intermediate receptacles (18, 22), said intermediate receptacles (18, 22) being connectable with the respective overpressure gas receptacles (15, 19), and reducing valves (16, 20) connected to the overpressure gas receptacles (15, 19) and being connectable with the respective intermediate receptacles (18, 20) for controlling supply of the test gases from the overpressure gas receptacles of the respective intermediate receptacles, said valve system including pneumatic change-over switches (17, 21) connected with the respective overpressure gas receptacles via the respective reducing valves, connected with the respective intermediate receptacles, and connected with the respiratory bag means, and operable for selectively connecting the respective overpressure gas receptacles with the respective intermediate receptacles via the respective reducing valves, and for selectively connecting the respective intermediate receptacles with the respiratory bag means.

6. Apparatus according to claim 1, with a respiratory tube (1) having said mouthpiece means thereon, means comprising said respiratory tube defining a respiratory passage leading from said mouthpiece means to said respiratory bag means, means (25, 27, 29) coupled with said respiratory passage for absorption of carbon dioxide from the respiratory gas exhaled into said respiratory passage and for the subsequent delivery of oxygen into the respiratory passage, whereby the density measuring means is operative to record the density of the gas mixture in the respiratory bag means during a complete test gas wash-in into the lungs.

7. Apparatus according to claim 1, with means for measurement of the final volume ($V_2$) of the gas in the respiratory bag means associated with the respiratory bag means.

8. Apparatus according to claim 1, with respiratory volume sensing means for connection with the mouthpiece means via said valve system, and recorder means for connection with said respiratory volume sensing means for recording respiratory volume curves.

9. Apparatus according to claim 8, with said recorder means being selectively connectable with said density measuring means and being operable for sequentially recording the respiratory volume curves and the density variation of gas within said respiratory bag means.

10. Apparatus for pulmonary function analysis, comprising:
respiratory bag means for receiving a test gas,
mouthpiece means for receiving the mouth of a patient,
a valve system controlling fluid connection of said mouthpiece means with said respiratory bag means,
gas supply means for supplying test gas to said respiratory bag means,
density measuring means coupled with respiratory bag means,
means for filling said respiratory bag means with a test gas from said gas supply means and for operating said density measuring means to register a test gas density value ($U_B$) representing the density of the test gas in said respiratory bag means, and
means comprising said valve system for connecting said mouthpiece means with said respiratory bag means after the filling thereof with said test gas and for operating said density measuring means to register a succession of values of the density of the test gas and respiratory air in said respiratory bag means as a patient inhales and exhales until an equilibrium value ($U_M$) of density is registered at said density measuring means, whereby in conjunction with a measured value of the density of room air ($U_L$), a measure of at least one of functional respiratory capacity (FRC) and residual volume (RV) is defined,
said density measuring means comprising an alternating flow generator having an output for supplying an alternating flow, a pressure sensor, and a hollow tube (6) extending into said respiratory bag means and coupled with the output of said generator for coupling the alternating flow from the generator with the gaseous medium within said respiratory bag means, said pressure sensor being coupled with said hollow tube between an end thereof within said respiratory bag means and an end thereof coupled with the output of said generator.

11. Apparatus for pulmonary function analysis, comprising:
respiratory bag means for receiving a test gas,
mouthpiece means for receiving the mouth of a patient,
a valve system controlling fluid connection of said mouthpiece means with said respiratory bag means,
gas supply means for supplying test gas to said respiratory bag means,
density measuring means coupled with respiratory bag means,
means for filling said respiratory bag means with a test gas from said gas supply means and for operating said density measuring means to register a test gas density value ($U_B$) representing the density of the test gas in said respiratory bag means, and
means comprising said valve system for connecting said mouthpiece means with said respiratory bag means after the filling thereof with said test gas and for operating said density measuring means to register a succession of values of the density of the test gas and respiratory air in said respiratory bag means as a patient inhales and exhales until an equilibrium value ($U_M$) of density is registered at said density measuring means, whereby in conjunction with a measured value of the density of room air ($U_L$), a measure of at least one of functional respiratory capacity (FRC) and residual volume (RV) is defined,
said gas supply means comprising a one-way cartridge which is pre-filled with a defined test gas quantity of a known concentration and overpressure, and said valve system comprising means for controlling the filling of the test gas into the respiratory bag means.

* * * * *